United States Patent [19]

Nakagawa

[11] Patent Number: 4,996,976
[45] Date of Patent: Mar. 5, 1991

[54] TONGUE DEPRESSOR WITH ILLUMINATING MEANS

[76] Inventor: Masahiko Nakagawa, 20-16, Oyamadai 2-chome, Setagaya-ku, Tokyo, Japan

[21] Appl. No.: 532,240

[22] Filed: May 30, 1990

Related U.S. Application Data

[63] Continuation of Ser. No. 291,784, Dec. 29, 1988, abandoned.

[30] Foreign Application Priority Data

Aug. 17, 1988 [JP] Japan .................................. 63-203288

[51] Int. Cl.⁵ .......................... A61B 1/06; A61B 13/00
[52] U.S. Cl. ........................................ 128/16; 362/32
[58] Field of Search ....................... 128/10, 11, 15, 16, 128/18; 362/32, 119

[56] References Cited

U.S. PATENT DOCUMENTS

| 2,690,745 | 10/1954 | Govan | 128/15 |
| 3,762,400 | 10/1973 | McDonald | 128/6 |
| 3,890,960 | 6/1975 | Wunsch, nee Kuhn et al. | 128/16 |
| 3,916,881 | 11/1975 | Heine | 128/16 |
| 4,320,745 | 3/1982 | Bhitiyakul et al. | 128/11 |
| 4,565,187 | 1/1986 | Soloway | 128/11 |
| 4,697,578 | 10/1987 | Burgn | 128/16 |
| 4,807,599 | 2/1989 | Robinson et al. | 128/16 |

FOREIGN PATENT DOCUMENTS

| 858235 | 11/1940 | France | 128/16 |
| 565548 | 8/1975 | Switzerland | 128/15 |

Primary Examiner—Edward M. Coven
Assistant Examiner—Mark Graham
Attorney, Agent, or Firm—Wenderoth, Lind & Ponack

[57] ABSTRACT

A tongue depressor includes a handle, a blade having one end thereof detachably fixed to the handle, and optical fibers fixed to the blade. The handle has a light source embedded therein for emitting light therefrom toward the optical fibers. The blade is made of a transparent resin. The light is transmitted through the optical fibers to illuminate the other end of the blade.

2 Claims, 6 Drawing Sheets

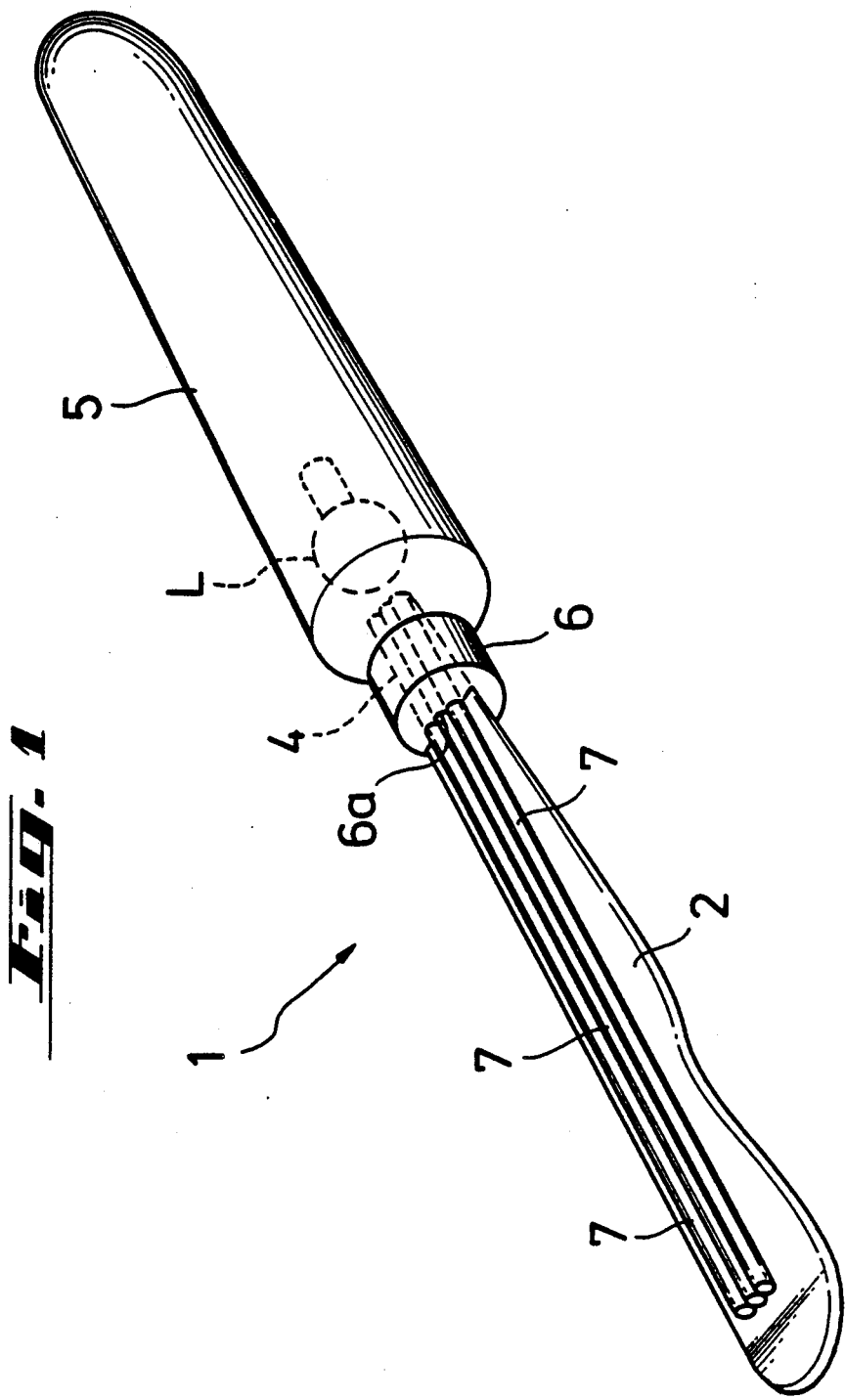

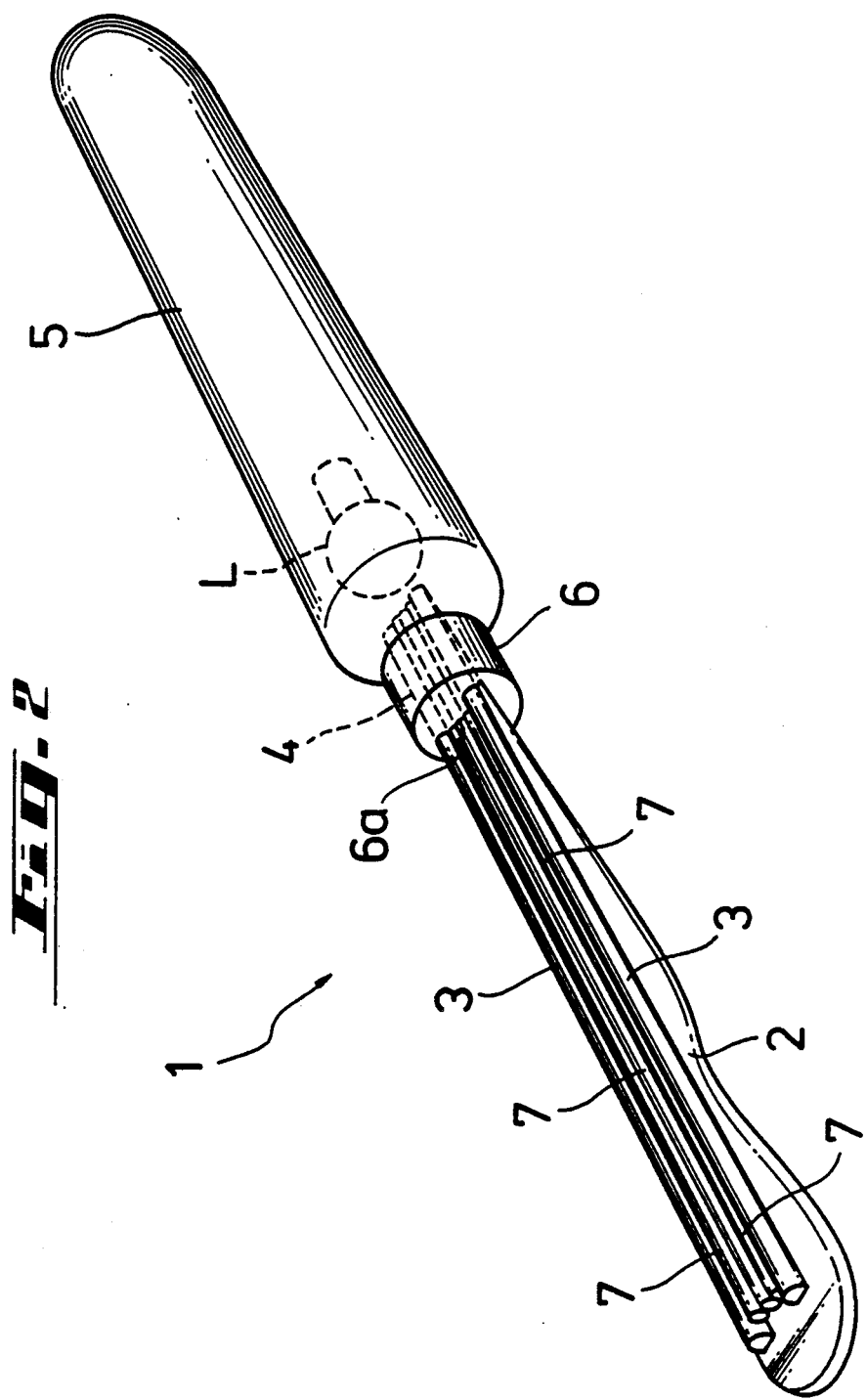

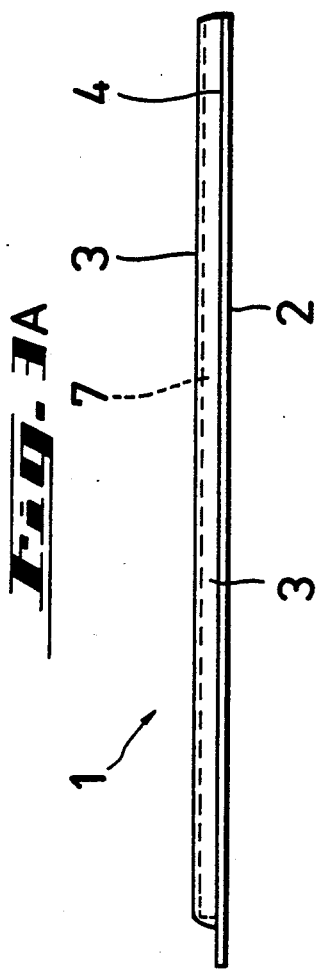
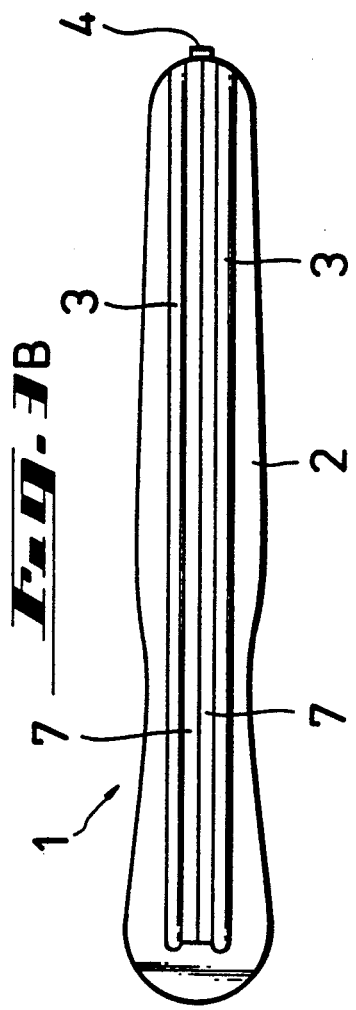
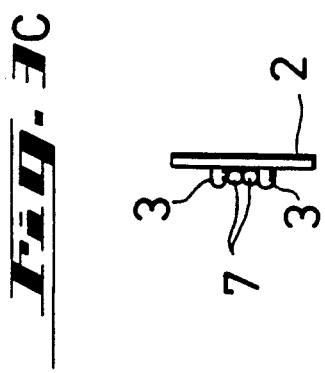

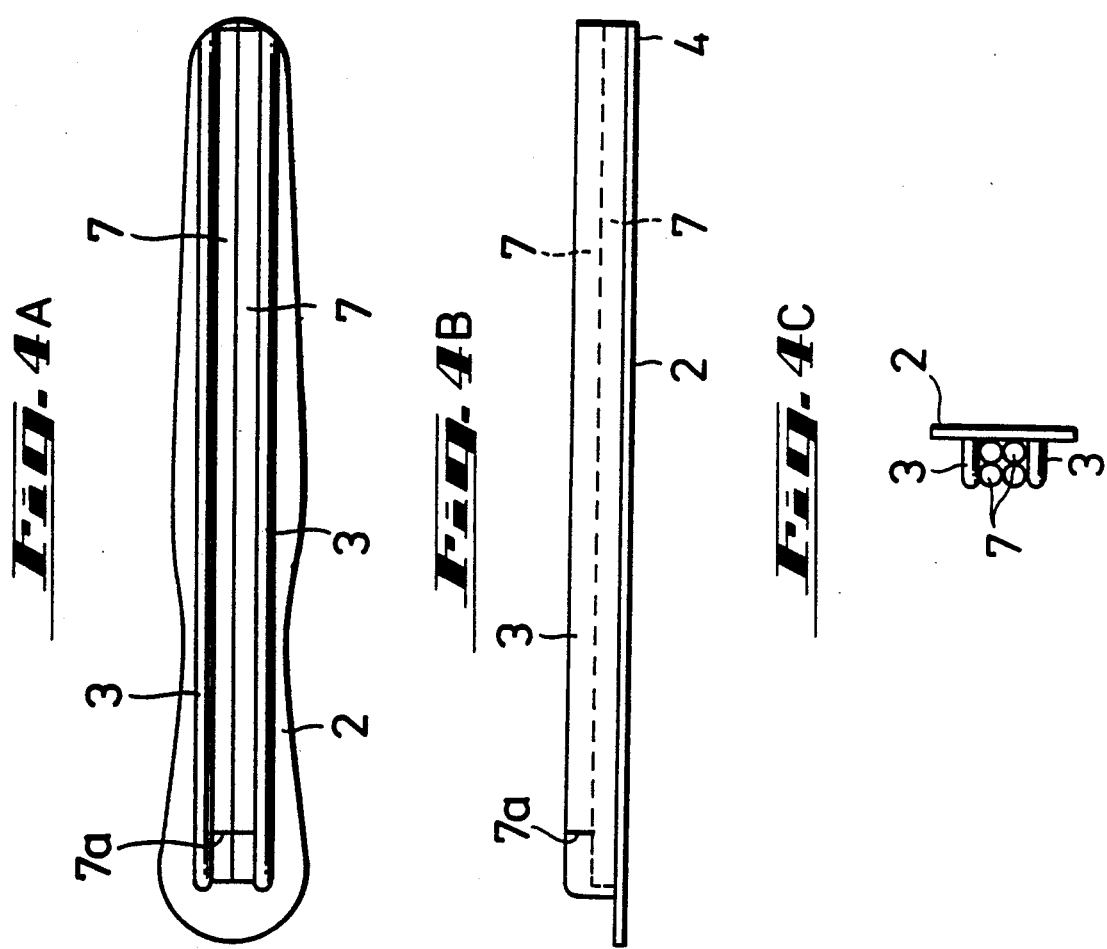

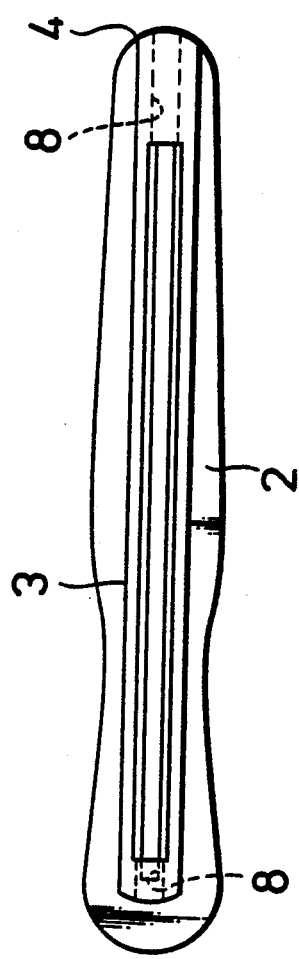
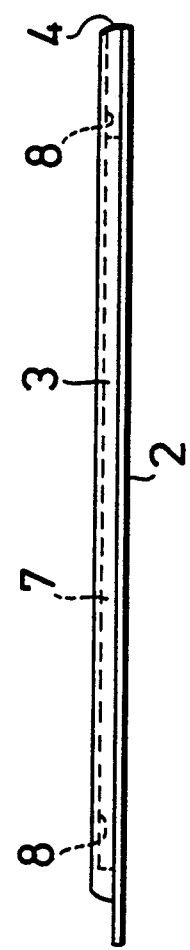
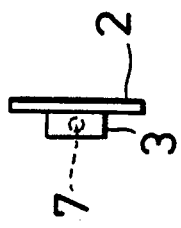
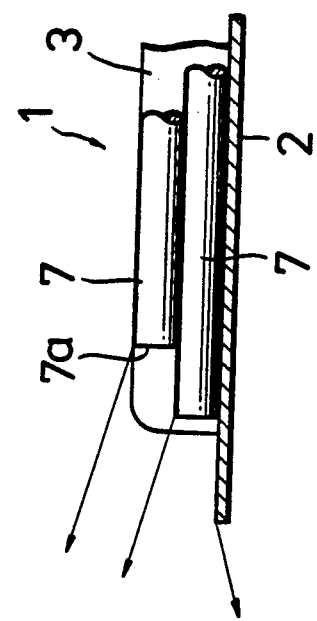

4,996,976

TONGUE DEPRESSOR WITH ILLUMINATING MEANS

This application is a continuation of now abandoned application Ser. No. 07/291,784 filed on Dec. 29, 1988.

BACKGROUND OF THE INVENTION AND RELATED ART STATEMENT

The present invention relates to a tongue depressor for making a diagnosis of the throat and the larynx, and more particularly, to a tongue depressor with illuminating means having a disposable blade.

Tongue depressors have been used for making a direct diagnosis of the throat and the larynx within the mouth. In recent years, the interior of the mouth has been illuminated by illuminating means provided on a tongue depressor instead of a reflector provided on the head of a doctor. Japanese Utility Model Public Disclosure No. 50-31787, for example, discloses a tongue depressor with means for illuminating the interior of the mouth which comprises a blade made of a light transmissible material coupled to a light source.

To be specific, as illustrated in FIG. 8, the prior art tongue depressor A comprises a main cylindrical body 70, illuminating means including an electric source 71 and a light source 72 provided within the main cylindrical body 70, an inner cylindrical body 73 for accommodating the light source 72 therein, and a light transmissible body 74 detachably supported within the inner cylindrical body 73. The light transmissible body 74 is made of a transparent hard material and has a bent free end. In use, an electric switch (not shown) is turned on to light the light source 72. As a result, the light emitted from the light source 72 is transmitted through the transparent light transmissible body 74 and sent out from the bent free end of the transparent light transmissible body 74. The throat and the larynx are thus subjected to diagnosis by illuminating the interior of the mouth with the light emitted from the bent free end of the transparent light transmissible body 74.

However, the prior art tongue depressor having the construction described above suffers from a great light transmission loss because the light transmissible body 74 is utilized as the optical path. In view of this loss, therefore, it is necessary to increase the light output. This will make the light source and tongue depressor large in size and complicated in shape and, consequently, the tongue depressor will be expensive to manufacture and be inconvenient to handle.

On the other hand, with the development of the medical safety technique, it has recently become desirable that medical instruments used in diagnosis be disposable. This desire can be fulfilled if the manufacturing cost is low, but has not yet been fulfilled for the reasons described above.

OBJECT AND SUMMARY OF THE INVENTION

An object of the present invention is to eliminate the drawbacks described above.

The main object of the present invention is to provide an inexpensive tongue depressor with illuminating means, which is light in weight and capable of transmitting the illuminating light with a high optical efficiency and which has a disposable blade.

To attain the object described above, according to the present invention, there is provided a tongue depressor with illuminating means comprising a handle having a light source embedded therein, a blade made of a transparent resin and having one end thereof detachably fixed to the handle, and optical fiber means fixed to the blade for transmitting light from the light source therethrough to illuminate the other end of the blade.

The above and other objects, characteristic features and advantages of the present invention will become more apparent to those skilled in the art as the disclosure is made in the following description of preferred embodiments of the invention, as illustrated in the accompanying drawings.

BRIEF DESCRIPTION OF THE DRAWINGS

FIG. 1 is a perspective view illustrating one embodiment of the tongue depressor with illuminating means according to the present invention.

FIG. 2 is a perspective view illustrating another embodiment of the tongue depressor with illuminating means according to the present invention.

FIGS. 3A, 3B and 3C are a side view, a plan view and a front view, respectively illustrating a blade of the tongue depressor of FIG. 2 having optical fiber means fixed thereto.

FIGS. 4A, 4B and 4C are a plan view, a side view and a front view, respectively illustrating another blade having optical fiber means fixed thereon.

FIG. 5 is an explanatory side view illustrating the light transmission of the optical fiber means of FIG. 4A.

FIGS. 6A, 6B and 6C are a plan view, a side view and a front view, respectively illustrating still another blade having optical fiber means fixed thereto.

DESCRIPTION OF THE PREFERRED EMBODIMENTS

Figure 7:
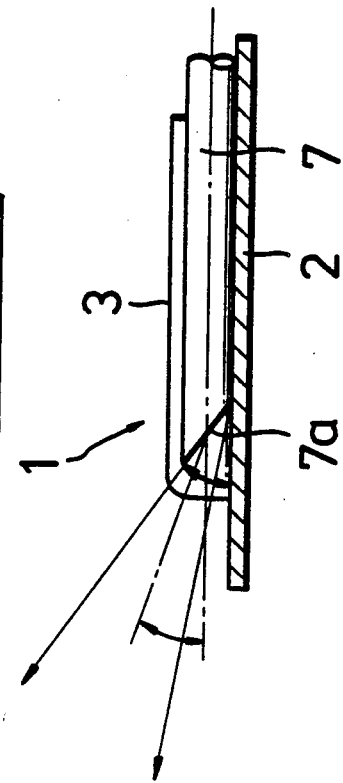
FIG. 7 is an explanatory side view illustrating light transmitting optical fiber means fixed to yet another blade.
Figure 8:
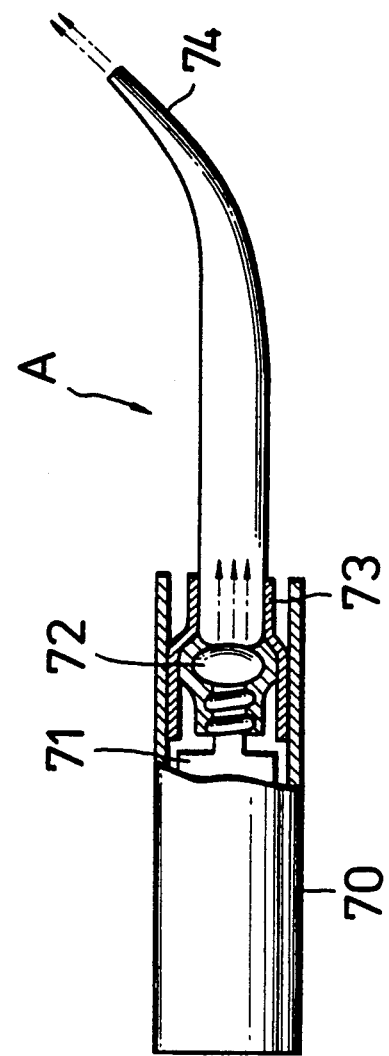
FIG. 8 is a partially cutaway side view illustrating a prior art tongue depressor.

The present invention will now be described with reference to the illustrated embodiments.

FIG. 1 is a perspective view illustrating one embodiment of the tongue depressor according to the present invention. In this embodiment, the tongue depressor 1 comprises a blade 2, a handle 5, a socket 6 attached to the handle 5 for connecting the blade 2 to the handle 5, optical fiber means disposed on and fixed to one surface of the blade 2, and illuminating means embedded in the handle 5. The blade 2 is made of a transparent resin, such as a styrene resin or an acryl resin, for example, in the form of a thin elongate plate having a base end 4 of a small width and a semicircular free end of a large width. The thickness of the blade 2 is about 1 mm, for example. The socket 6 has a slot 6a formed therein for detachably admitting the base end 4a of the blade 2. The illuminating means includes an electric bulb L as a light source, an electric source (not shown) and a switch (not shown). The optical fiber means in this embodiment comprises a plurality of optical fibers 7 which are slightly shorter in length then the blade 2 and are disposed on and fixed to one surface of the blade 2, with their end faces on the light-receiving sides thereof aligned with the end face of the base end 4 of the blade 2 and with their end faces on the light-emitting sides thereof not reaching the free end of the blade 2. Each of the optical fibers 7 made be made of quartz, multicomponent glass or plastic, for example, in the form of a rod or the like and may be of a single-mode type, multimode type, graded index type or fluorescent type, for example. The socket 6 may be either integral with or separate from the handle 5. When the socket 6 is a separate member, it is fixed to the handle 5 by fixing means such as screw means, for example.

With the tongue depressor 1 of the construction described above, the light from the electric bulb L is received by the light-receiving ends of the optical fibers 7, transmitted through the optical fibers 7 and emitted from the light-emitting ends of the optical fibers 7. Part of the light emitted from the light-emitting ends of the optical fibers 7 is transmitted into and sent out from the free end of the blade 2. Therefore, the throat etc. can be efficiently illuminated in a wide range with the light emitted directly from the light-emitting ends of the optical fibers 7 and emitted through the free end of the blade 2. Furthermore, the blade 2 having the optical fibers 7 fixed thereto is detachably fixed to the handle 5 through the socket 6 and, therefore, the blade 2 once used can be replaced by a new one. This is very advantageous in attaining sanitary conditions.

FIGS. 2 and 3A to 3C illustrate another embodiment of the tongue depressor according to the present invention. The optical fiber means comprises three optical fibers 7 in FIG. 2 and two optical fibers 7 in FIGS. 3A to 3C. In this embodiment, a pair of ribs 3 are provided on one surface of the blade 2 and the optical fiber means is interposed therebetween for the purpose of reinforcing the mechanical strength of the blade 2 and preventing the optical fibers 7 from movement in the direction of the width of the blade 2. The ribs 3 are slightly shorter in length than the blade 2 and are substantially similar in length or slightly larger than the optical fibers 7. The ribs 3 also have a height substantially the same as or slightly greater than the diameter of the optical fibers 7. The construction of this embodiment other than that described above is the same as that of the preceding embodiment.

FIGS. 4A to 4C and 5 show another example of the blade 2, in which the optical fiber means comprises two lower optical fibers 7 and two upper optical fibers 7 superposed on the lower optical fibers 7. The upper optical fibers 7 are shorter than the lower optical fibers 7 and have their light-emitting ends 7a further away from the free end of the blade 2 than the light-emitting ends of the lower optical fibers 7, thereby increasing the angle at which the light is emitted from the light-emitting ends of the optical fibers 7 as shown in FIG. 5. In this example, the height of the ribs 3 is substantially twice the diameter of the optical fibers 7 as illustrated in FIG. 4C.

In place of the optical fibers 7 disposed in two stages in a staircase fashion as shown in FIG. 5, an optical fiber 7 having an upwardly inclined light-emitting end face 7b as shown in FIG. 7 may be used to obtain, similarly to the case shown in FIG. 5, an increased angle at which the light is emitted.

FIG. 6A shows still another example of the blade 2, in which a single reinforcing rib 3 having a through hole 8 open at opposite ends of the rib 3 is provided on the blade 2. The optical fiber means comprising a single optical fiber 7 is inserted under pressure into the through hole 8 and fixed therein.

The through hole 8 formed in the rib 3 may be closed at the light-emitting end of the optical fiber 7, as shown in FIG. 6B, and an optical fiber 7 is inserted from the base end 4 of the blade 2 into the through hole 8. In this case, the light transmitted through the optical fiber 7 is widely spread and provides a mellow light through the blade 2.

When the blade 2 has a large thickness, a groove (not shown) is formed in one surface of the blade 2 in the lengthwise direction for locating the optical fiber means therein. In this case, the reinforcing rib may be omitted. Furthermore, in the case of the blade 2 shown in FIG. 6A or FIG. 6B, the free end of the blade 2 may be bent.

As has been described in the foregoing, according to the present invention, the light from the light source embedded in the handle is transmitted through the optical fiber means and emitted from the light-emitting ends of the optical fiber means at the free end of the blade. The light thus repeats total reflection within the optical fiber means and is efficiently emitted with very small loss or attenuation of light.

Furthermore, in the present invention, since the blade is detachably fixed to the handle, after it is once used, it can be detached and interchanged with another one. This is advantageous in attaining sanitary conditions. If a plurality of blades of the various kinds illustrated in the accompanying drawings are prepared, the one most desirable in view of the particular diagnostic conditions can be selected for use.

What is claimed:

1. A tongue depressor comprising:
    a handle having a light source embedded therein;
    a transparent resin blade having first and second ends, said first end being detachably fixed to said handle;
    optical fiber means, for transmitting light from said light source to said second end of said blade, comprising a plurality of optical fibers fixed longitudinally along said blade, each having a light-receiving end fixed to said first end of said blade and a light-emitting end spaced from said second end of said blade toward said first end of said blade, said plurality of optical fibers comprising lower optical fibers and upper optical fibers superposed on said lower optical fibers, said light-emitting end of each of said upper optical fibers being spaced farther from said second end of said blade than said light-emitting end of each of said lower optical fibers; and
    means, for preventing lateral movement of said plurality of optical fibers, comprising a pair of support ribs extending longitudinally along said blade and closely confining said plurality of optical fibers therebetween.

2. A tongue depressor as recited in claim 1, further comprising
    socket means, connected to said handle, for releasably receiving said blade to thereby connect said blade to said handle.

* * * * *